United States Patent
Affagard et al.

(10) Patent No.: US 10,980,839 B2
(45) Date of Patent: Apr. 20, 2021

(54) METHOD OF PREPARING A FAECAL MICROBIOTA SAMPLE

(71) Applicants: MAAT PHARMA, Lyons (FR); INSTITUT NATIONAL DE LA RECHERCHE AGRONOMIQUE, Paris (FR)

(72) Inventors: Hervé Affagard, Lyons (FR); Carole Schwintner, Lyons (FR); Catherine Juste, Le Perray-en-Yvelines (FR); Joël Dore, Vitry sur Seine (FR); Patricia Lepage, Paris (FR); Christel Maillet, Saclay (FR); Sylvie Rabot, Senlisse (FR); Fernanda Fonseca, Villepreux (FR); Hervé Blottiere, Nantes (FR)

(73) Assignees: MAAT PHARMA, Lyons (FR); INSTITUT NATIONAL DE RECHERCHE POUR L'AGRICULTURE, L'ALIMENTATION ET L'ENVIRONNEMENT, Paris (FR)

( * ) Notice: Subject to any disclaimer, the term of this patent is extended or adjusted under 35 U.S.C. 154(b) by 0 days.

(21) Appl. No.: 15/568,838

(22) PCT Filed: Apr. 22, 2016

(86) PCT No.: PCT/FR2016/050958
§ 371 (c)(1),
(2) Date: Oct. 24, 2017

(87) PCT Pub. No.: WO2016/170285
PCT Pub. Date: Oct. 27, 2016

(65) Prior Publication Data
US 2018/0099012 A1    Apr. 12, 2018

(30) Foreign Application Priority Data
Apr. 24, 2015  (FR) ...................... 15 53716

(51) Int. Cl.
| | | |
|---|---|---|
| *A61K 35/38* | (2015.01) | |
| *A61K 35/74* | (2015.01) | |
| *A61K 9/19* | (2006.01) | |
| *A61K 35/741* | (2015.01) | |
| *A61P 1/00* | (2006.01) | |
| *A01N 1/02* | (2006.01) | |
| *A61K 47/26* | (2006.01) | |
| *A61K 35/00* | (2006.01) | |
| *A61K 9/107* | (2006.01) | |

(52) U.S. Cl.
CPC ............ *A61K 35/38* (2013.01); *A01N 1/0221* (2013.01); *A01N 1/0284* (2013.01); *A61K 9/19* (2013.01); *A61K 35/74* (2013.01); *A61K 35/741* (2013.01); *A61P 1/00* (2018.01); *A61K 9/107* (2013.01); *A61K 47/26* (2013.01); *A61K 2035/115* (2013.01)

(58) Field of Classification Search
CPC .......... A61K 35/38; A61K 9/19; A61K 35/74; A61K 35/741; A61K 9/107; A61K 47/26; A61K 2035/115; A61P 1/00; A01N 1/0221; A01N 1/0284
USPC ....................................................... 424/93.3
See application file for complete search history.

(56) References Cited

U.S. PATENT DOCUMENTS

| | | | | |
|---|---|---|---|---|
| 7,858,336 | B1 * | 12/2010 | Garner ...................... | C12R 1/23 435/41 |
| 2012/0064606 | A1 * | 3/2012 | Cho ........................ | C12M 47/10 435/252.9 |
| 2014/0341873 | A1 * | 11/2014 | Chen .................... | A61K 35/742 424/93.45 |
| 2015/0037285 | A1 | 2/2015 | Blaser et al. | |

FOREIGN PATENT DOCUMENTS

| | | |
|---|---|---|
| WO | 02/07741 | 1/2002 |
| WO | 2011122949 | 10/2011 |
| WO | 2012/016287 | 2/2012 |
| WO | 2012/122478 | 9/2012 |

(Continued)

OTHER PUBLICATIONS

Kuntz, Bulking Agents: Bulking Up While Scaling Down, Natural Products Insider, Jun. 1996, Available Online at: www.naturalproductsinsider.com/specialty-nutrients/bulking-agents-bulking-while-scaling-down.*

Everard, et al., Cross-talk between Akkermansia muciniphila and intestinal epithelium controls diet-induced obesity, Proc. Natl. Acad. Sci, USA, May 2013, pp. 9066-9077, vol. 110, No. 22.

(Continued)

*Primary Examiner* — Jennifer M. H. Tichy
(74) *Attorney, Agent, or Firm* — Browdy and Neimark, PLLC

(57) ABSTRACT

The present invention relates to a method for preparing a fecal 5 microbiota sample of a donor subject. Said method includes the following steps: a) collecting at least one fecal microbiota sample from the donor subject; b) within a period of less than 5 minutes after collecting the sample, placing said sample obtained in step a) in an oxygen-tight collection device; c) mixing the sample obtained in step b) with at least one aqueous saline 10 solution containing at least one cryoprotectant and/or a filling agent; d) optionally, filtering the mixture obtained in step c), in particular by means of a filter comprising pores having a diameter of less than or equal to 0.7 mm, preferably less than or equal to 0.5 mm; and e) storing the mixture obtained in step c) or d) by freezing said mixture at a temperature 15 of between −15° C. and −100° C. Steps b) to e) are carried out in anaerobiosis.

15 Claims, 2 Drawing Sheets

(56) References Cited

FOREIGN PATENT DOCUMENTS

Figure 1:
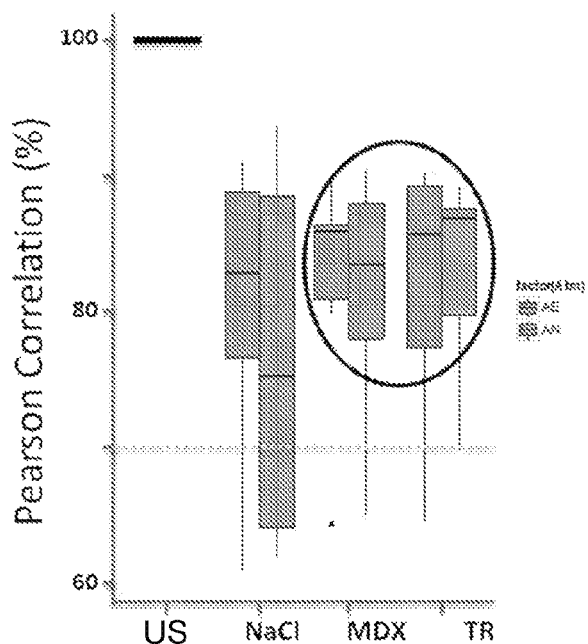

| WO | WO 2014/029758 | * | 2/2014 |
|----|----------------|---|--------|
| WO | 2014/078911 | | 5/2014 |
| WO | 2014/121298 | | 8/2014 |
| WO | 2014/121301 | | 8/2014 |
| WO | 2014/121302 | | 8/2014 |
| WO | 2014/121304 | | 8/2014 |
| WO | WO 2014/152484 | * | 9/2014 |
| WO | 2014/176632 | | 11/2014 |
| WO | 2014/197562 | | 12/2014 |
| WO | 2016/201114 | | 12/2016 |
| WO | 2017/075098 | | 5/2017 |

OTHER PUBLICATIONS

Sokol, et al., Faecalibacterium prausnitzii is an anti-inflammatory commensal bacterium identified by gut microbiota analysis of Crohn disease patients, Proc. Natl. Acad. Sci. USA, Oct. 2008, pp. 16731-16736, vol. 105 No. 43.

Tauxe, et al., Fecal Microbiota Transplant Protocol for Clostridium Difficile Infection, Lab Med., 2015, pp. 1-8, vol. 46 (1).

Prakash et al., Practice and prospects of microbial preservation, FEMS Microbiol Lett, 339:1-9 (2013).

Semyonov et al., Microenxapsulation of Lactobacillus paracasei by spray freeze drying, Food Research International, 43:193-202 (2010).

* cited by examiner

METHOD OF PREPARING A FAECAL MICROBIOTA SAMPLE

The present invention relates to a method of preparing a faecal microbiota sample. The invention also relates to the use of said sample in the transplantation of faecal microbiota, preferably for treating intestinal dysbioses, in particular infections of *Clostridium difficile*.

Human intestinal microbiota is the group of all microorganisms (bacteria, yeast and fungi) to be found in the human gastro-intestinal tract (stomach, intestine and colon).

The microbial diversity is currently estimated at about $10^3$ bacterial species composing the dominant intestinal microbiota of an adult individual, with an abundance of $10^{14}$ bacteria, representing a bacterial metagenome of 200 000 to 800 000 genes in each individual, which is 10 to 50 times the number of genes of the human genome.

The intestines are sterile in utero and are colonized as of the first days of life to develop towards a unique individual microbiota. Each person has bacteria that are relatively close in terms of species, but the exact composition of his or her microbiota (species, proportions) is to a large extent (more than ⅔ of the species) specific to the host.

Thus, the human intestinal microbiota is a very diversified ecosystem, which is complex and specific to each individual.

It is essential for the health of an individual to maintain a stable microbiota which is both capable of returning to its initial state after a change and resistant to invasion.

Maintaining a wide diversity of microbiota promotes its stability. However, certain pathologies or treatments unbalance the microbiota: antibiotics for example, as well as diseases with an inflammatory component, such as inflammatory bowel diseases (IBDs), can limit the diversity of the microbiota in the intestines.

Antibiotics treatments (or antibiotic therapy), in particular, result in an alteration of the microbiota, which can promote the proliferation of pathogenic organisms such as *Clostridium difficile*.

Infections of *Clostridium difficile* are responsible for nosocomial diarrhea; this bacterium is resistant to conventional antibiotic therapy (of broad spectrum, such as vancomycin or metronidazole). In order to reestablish the intestinal microbiota, and fight against infections of *Clostridium difficile* type, and thereby reestablish homeostasis (i.e. symbiosis), the transplantation of faecal microbiota has been envisioned and tested.

It consists in the introduction of the stools of a healthy donor subject into the digestive tract of a recipient patient, in order to re-balance the altered intestinal microbiota of the host. This transplantation of faecal microbiota can be allogenic (that is to say from a healthy donor individual to a patient) or autologous (that is to say from an individual to himself). The results obtained on infections of *Clostridium difficile* type are encouraging, and some patients have been successfully treated (Tauxe et al, Lab Medicine, Winter 2015, volume 46, Number 1).

However, the current transplantation method is empirical and takes no particular precaution to preserve as best possible the viability of the anaerobic bacteria, which are the majority component of the intestinal microbiota. Furthermore, the effectiveness of the faecal microbiota transplantation is variable, and may require more than one treatment. Furthermore, allogenic transplantation requires testing the faeces of the donor to check that no pathogenic germ will be transported to the recipient, or will present a risk for the staff manipulating it during the operation.

There is thus a need to have a method of transplanting faecal microbiota which is safe, effective and easy to implement, in particular at industrial scale. Furthermore, there is a need for a method of transplanting faecal microbiota in which the viability of the bacteria is mentioned.

The present invention enables these needs to be addressed.

The present invention thus relates to a method of preparing a sample of faecal microbiota from a donor subject, comprising the following steps:

a) taking at least one sample of faecal microbiota from the donor subject, b) within 5 minutes following taking of the sample, placing said sample obtained in a) in an oxygen-tight collecting device, c) mixing the sample obtained in b) with at least one saline aqueous solution comprising at least one cryoprotectant and/or at least one bulking agent, d) optionally, filtering the mixture obtained in c), in particular using a filter comprising pores of diameter less than or equal to 0.7 mm, preferably less than or equal to 0.5 mm and e) storing the mixture obtained in c) or d) by freezing at a temperature between −15° C. and −100° C., preferably between −60° C. and −90° C., steps b) to e) being carried out under anaerobiosis.

Such a method of transplanting faecal microbiota is indeed easy to implement, and its effectiveness may be estimated by comparing the microbial population obtained after performing the method, compared with the initial sampling. Various indicia may be used to evaluate this effectiveness, and the following results have been obtained:

| Indicia | Bray-Curtis dissimilarity | Canberra Distance | Jaccard Index | Jensen-Shannon Divergence | Morisita's index | Pearson correlation coefficient |
|---|---|---|---|---|---|---|
| Family | <0.4 | <0.7 | <0.6 | <0.4 | <0.5 | >0.7 |
| Genus | <0.5 | <0.7 | <0.7 | <0.4 | <0.6 | >0.5 |
| OTU | <0.7 | <0.9 | <0.8 | <0.4 | <0.7 | >0.3 |

The present invention also relates to the use of a sample of fecal microbiota from a donor subject capable of being obtained by the method according to the invention, in the thawed state, in the transplantation of autologous or allogenic faecal microbiota.

The present invention also relates to the use of a sample of faecal microbiota from a donor subject capable of being obtained by the method according to the invention, in the thawed state, for treating intestinal dysbioses, and in particular infections of *Clostridium difficile*, dysbioses induced by medical treatments, by physical treatments (radiation in particular), by surgical operations (in particular intestinal), or by the provision of nutrition. The present invention also relates to the use of a sample of faecal microbiota from a donor subject capable of being obtained by the method according to the invention, in the thawed state, for treating a pathology chosen from inflammatory bowel diseases (IBDs), functional disorders of the intestines, obesity, metabolic diseases (type-2 diabetes and metabolic syndrome in particular) and auto-immune diseases (type-1 diabetes in particular), allergies, hepatic diseases (fatty liver and cirrhosis in particular), certain neurological diseases (autism in particular) and certain cancers (colorectal cancer in particular).

By intestinal dysbiosis is meant any sustained imbalance of the intestinal microbiota. By sustained imbalance of the intestinal microbiota is meant any loss of beneficial microorganisms, and/or any loss in diversity of microorganisms, and/or any expansion or development of aggressive microorganisms among the commensals (pathobionts), and/or any proliferation of pathogenic microorganisms (*C. difficile* in particular). Any sustained alteration of the human intestinal microbiota may indeed engender a pathological state. In particular, the reduction of diversity among the microbiota is characteristic of diseases associated with dysbiosis (obesity, Crohn's disease, diabetes or allergy in particular) (Sansonetti, College de France, 22 Jan. 2014).

Preferably, the pathology to treat is an intestinal dysbiosis.

By inflammatory bowel diseases (IBDs) is meant in particular Crohn's disease and ulcerative colitis.

By functional disorders of the intestines, is meant in particular irritable bowel syndrome and spastic colitis.

The method of preparing a sample of faecal microbiota from a donor subject according to the invention thus comprises a step a) of taking at least one sample of faecal microbiota from the donor subject.

This step is preferably carried out by taking a sample of stools from the donor subject.

As a matter of fact, the sample of stools contains faecal microbiota from the donor subject. Thus, the method according to the invention comprises a step a) of taking at least one sample of stools, comprising the faecal microbiota, from the donor subject.

Preferably, according to the invention, the donor subject is a healthy human subject. By "healthy" is meant a subject not suffering from an imbalance in the intestinal microbiota or from a pathology diagnosed/recognized by the medical profession.

Preferably, the sample of stools has a mass of at least 20 g.

Further to this sampling step, and within a very short time, i.e. less than 5 minutes following the taking of the sample, preferably less than 3 minutes, more preferably less than 1 minute, the sample obtained in a) is placed in an oxygen-tight collecting device: this is step b).

The whole of the rest of the method is henceforth carried out under anaerobiosis (i.e. in an anaerobic atmosphere).

Preferably, the air-tight collecting device takes a form of the type comprising:
  a container comprising a body which comprises an internal space configured to receive the sample of faecal microbiota from the donor subject, and a neck which delimits an access opening to the internal space of the body, and
  a cover configured to be removably and sealingly mounted on the neck of the container so as to obturate the access opening of the neck and close the internal space of the body,
  wherein the body of the container is constituted by a flexible bag, and wherein at least one of the container and the cover is provided with an evacuation member configured for evacuating at least part of the gases contained in the internal space of the body of the container.

Preferably, the evacuation member of the device comprises a passage provided through one of the container and the cover, and an obturating member for obturating the passage to prevent external fluids from entering the internal space of the container body.

Preferably, the evacuation member of the device further comprises a microporous filter membrane disposed in the passage.

Alternatively, the air-tight collecting device takes a form of the type comprising:
  a container comprising a body which comprises an internal space configured to receive the sample of faecal microbiota from the donor subject, and a neck which delimits an access opening to the internal space of the body, and
  a cover configured to be removably and sealingly mounted on the neck of the container so as to obturate the access opening of the neck and close the internal space of the body,
  wherein the internal space of the body of the container possibly comprises a chemical device neutralizing the oxygen.

Preferably, the air-tight collecting device is used for steps a) and b): the taking of the sample of step a) being carried out directly in said device, in particular in the container, and the closing of the device, in particular by virtue of the cover, places the sample in an atmosphere without oxygen (step b).

According to the method of the invention, steps b) to e) are carried out in an oxygen-free atmosphere. Under anaerobiosis, the viability of the bacteria constituting the faecal microbiota and present in the sample is thereby preserved.

In particular, the device used at step b), mentioned above, enables all the steps b) to e) to be carried out under anaerobiosis.

Once the sample (obtained in a) has been placed in an oxygen-tight collecting device, it may, optionally, be incubated at a temperature comprised between 33° C. and 40° C. for a maximum time of 75 h. Preferably this incubation step is carried out at a temperature comprised between 35° C. and 38° C., for a time comprised between 24 h and 73 h. Ideally, this step is carried out at a temperature of approximately 37° C. for 72 h. Alternatively, the sample may, optionally, be incubated at a temperature comprised between 2° C. and 10° C. for a maximum time of 75 h. Preferably this incubation step is carried out at a temperature comprised between 4° C. and 8° C., for a time comprised between 24 h and 72 h.

After this step, a visual inspection may be made, in order to evaluate the quality of the sample obtained at this stage of the method. If the inspection is satisfactory, optionally, a transportation step may thus take place. This transportation step enables the sample to be brought back from the location of sampling to the laboratory, for later treatment and analysis. The visual inspection mentioned above may also be carried out after the transport.

Thus, preferably, the sample placed in the collecting device of step b) undergoes a transportation step prior to step c).

Preferably too, the sample placed in the collecting device of step b) is incubated at a temperature comprised between entre 33° C. and 40° C., preferably between 35° C. and 38° C., for a maximum time of 75 h, preferably comprised between 24 h and 73 h, between steps b) and c). Preferably, the incubation takes place before and during the transportation step.

Step c) occurs next: this step comprises mixing the sample obtained in b) with at least one saline aqueous solution comprising at least one cryoprotectant and/or at least one bulking agent.

If a transportation step, and possibly an incubation step, take place, then step c) of course comprises mixing the sample obtained in b), after transportation and/or incubation, with at least one saline aqueous solution comprising at least one cryoprotectant and/or at least one bulking agent.

Typically, the saline aqueous solution according to the invention comprises water and physiologically acceptable salts. Typically, the salts are salts of calcium, sodium, potassium or magnesium, with chloride, gluconate, acetate or hydrogen carbonate ions.

The saline aqueous solution according to the invention may also optionally comprise at least one antioxidant. The antioxidant is in particular chosen from ascorbic acid and its salts (ascorbate), tocopherols (acid α-tocopherol), cysteine and its salt forms (hydrochloride in particular) and mixtures of these.

Preferably, the saline aqueous solution according to the invention comprises:
  at least one salt chosen from sodium chloride, calcium chloride, magnesium chloride, potassium chloride, sodium gluconate and sodium acetate, and
  optionally at least one antioxidant, preferably chosen from sodium L-ascorbate, tocopherols, L-cysteine hydrochloride monohydrate and mixtures of these.

Typically, salt is present in the saline aqueous solution at a concentration comprised between 5 and 20 g/L, preferably between 7 and 10 g/L.

Typically, the antioxidant is present in the saline aqueous solution in an amount comprised between 0.3 and 1% by weight relative to the total volume of solution, preferably between 0.4% and 0.6% by weight relative to the total volume of solution.

Preferably, when the antioxidant is a mixture of sodium L-ascorbate and L-cysteine hydrochloride monohydrate, the sodium L-ascorbate is present in an amount comprised between 0.4 and 0.6% by weight relative to the total volume of solution, and the L-cysteine hydrochloride monohydrate is present in an amount comprised between 0.01 and 0.1% by weight relative to the total volume of solution.

Preferably, the saline aqueous solution according to the invention also comprises at least one cryoprotectant. A cryoprotectant is a substance used to protect the sample from damage caused by freezing, in particular due to the formation of ice crystals.

Preferably, the cryoprotectant is chosen from polyols, di- to pentasaccharides (i.e. disaccharides, trisaccharides, quadrisaccharides and pentasaccharides), DMSO and mixtures of these. Preferably, the cryoprotectant is chosen from polyols, tri- and disaccharides, DMSO and mixtures of these. More preferably, cryoprotectant present in the saline aqueous solution is a disaccharide or a trisaccharide.

Among the polyols that may be used are in particular not only glycerol, mannitol, and sorbitol, but also propylene glycol or ethylene glycol.

Among the di- to pentasaccharides that may be used, it is possible to cite dimers, trimers, quadrimers and pentamers with identical or different units, said units being chosen from glucose, fructose, galactose, fructose and N-acetyl-neuraminic acid.

Among the disaccharides that may be used are in particular trehalose or one of its analogs, or saccharose.

Lastly, DMSO, or dimethylsulfoxide, is a conventional cryoprotectant.

These cryoprotectants may be used alone or in a mixture.

Typically, the total amount of cryoprotectant present in the saline aqueous solution is comprised between 3 and 30% by weight relative to the total volume of solution, preferably between 4% and 20% by weight relative to the total volume of solution.

Preferably, the cryoprotectant is chosen from glycerol, mannitol, sorbitol, DMSO, propylene glycol, ethylene glycol, trehalose and its analogs, saccharose, galactose-lactose and mixtures of these. Preferably, the cryoprotectant is galactose-lactose or trehalose.

Preferably, the saline aqueous solution according to the invention comprises at least one bulking agent.

The bulking agent is preferably chosen from partial hydrolysates of starch or starchy flour. The partial hydrolysates of starch, preferably from wheat or maize, as well as the partial hydrolysates of starchy flour, for example from potatoes, comprise a high amount of maltodextrins. Maltodextrins are the result of the partial hydrolysis of starch or starchy flour, and are constituted by various sugars (glucose, maltose, maltotriose, oligo- and polysaccharides), of which the proportions vary according to the degree of hydrolysis.

Preferably, the bulking agent present in the saline aqueous solution is a mixture of maltodextrins, in which the amount of maltodextrins is comprised between 4 and 20% by weight relative to the total volume of solution.

Preferably, the saline aqueous solution according to the invention comprises both:
  at least one cryoprotectant as described above, i.e. chosen from polyols, di- to pentasaccharides (i.e. disaccharides, trisaccharides, quadrisaccharides and pentasaccharides), DMSO and mixtures of these, and
  at least one bulking agent as described above, i.e. chosen from partial hydrolysates of starch or starchy flour, preferably the bulking agent is constituted by maltodextrins.

Preferably, in this case, the total amount of cryoprotectant is comprised between 3 and 30% by weight relative to the total volume of solution, preferably between 4% and 20% by weight relative to the total volume of solution; and the amount of bulking agent, preferably maltodextrins, is comprised between 4 and 20% by weight relative to the total volume of solution.

Step c) of mixing the sample obtained in b) with at least one saline aqueous solution comprising at least one cryoprotectant may in particular be carried out by kneading, in order to obtain a homogenous mixture.

Preferably, the sample obtained in b) is mixed with said saline aqueous solution in a respective weight/volume ratio comprised between 0.5 weights: 10 volumes and 2 weights: 2 volumes. A sample: solution weight/volume ratio equal to 0.5 weights: 10 volumes means that the sample is mixed in an amount of 0.5 weights (for example 0.5 g) for 10 volumes of solution (for example 10 ml). Preferably, the sample: solution weight/volume ratio is equal to 1 sample weight for 4 volumes of solution (1 weight: 4 volumes).

Once this step has been carried out, an optional step d) can be performed. Step d) comprises filtering the mixture obtained in c), in particular using a filter comprising pores of diameter less than or equal to 0.7 mm, preferably less than or equal to 0.5 mm. Such filtration enables coarse particles to be retained, and the bacteria of interest to be collected (constituting the faecal microbiota) in the filtrate.

Next, further to step c) or d), where the latter is implemented, the mixture obtained is stored by freezing at a temperature between −15° C. and −100° C.: this is step e). Preferably, the temperature of freezing (and thus of storage) is comprised between −60° C. and −90° C.; more preferably it is approximately −80° C. or about −65° C.

In order to be frozen, further to step c) or d), and before step e) the mixture may be divided into aliquots, to provide specimens of uniform volume. For example; the division into aliquots is carried out to obtain specimens of volume equal to 50 ml, 100 ml, 150 ml, or 200 ml. Preferably the division into aliquots is carried out to obtain specimens of volume equal to 100 ml.

This step of freezing and storage enables the treated samples to be kept for a period of at least 2 months. The samples stored in this way are moreover of good quality, even after thawing.

Preferably, the method according to the invention comprises a step f) of thawing the frozen sample obtained in e), under anaerobiosis, up to ambient temperature. This thawing step f) can be carried out by placing the frozen sample in a water bath at a temperature comprised between 35° C. and 40° C., for example 37° C., for a period of a few minutes (typically from 2 to 10 minutes) Thawing step f) can also be carried out by placing the frozen sample at a temperature comprised between 2° C. and 10° C., for example between 4° C. and 8° C., for a period from 10 to 20 hours.

The sample thus thawed, at ambient temperature, may then be administered to the recipient patient.

The recipient patient may be different from the donor subject, and the transplantation is then allogenic.

The recipient patient can also be identical to the donor subject, and the transplantation is then autologous; this type of transplantation may take place when the subject, then healthy, gives a sample before alteration of his or her microbiota. The sample is then frozen according to the steps described in the present application, then transplanted into that same subject (recipient patient) if the latter presents in particular an infection of *Clostridium difficile*. The autologous transplantation of faecal microbiota presents the advantage of avoiding the transmission of a pathogenic agent coming from another donor.

The present invention also relates to a sample of fecal microbiota from a donor subject capable of being obtained by the method according to the invention, for its use, in the transplantation of autologous or allogenic faecal microbiota.

The present invention also relates to a sample of fecal microbiota from a donor subject capable of being obtained by the method according to the invention, for its use for treating the infections of *Clostridium difficile*. The present invention also relates a sample of faecal microbiota from a donor subject capable of being obtained by the method according to the invention, for its use for treating a pathology chosen from inflammatory bowel diseases (IBDs), functional disorders of the intestines, obesity, metabolic diseases and auto-immune diseases, allergies, neurological diseases and cancers.

The invention will now be exemplified using the following examples, which are not limiting.

The captions of the drawings are the following:

FIG. 1: Pearson correlation for phylo-transcriptomic sequencing
US. untreated faecal sample (not processed) control
NaCl. Saline solution
MDX. Saline with maltodextrins 15% (w/v)+trehalose 5% (w/v)
TR. Saline with trehalose 15% (w/v)+maltodextrins 5% (w/v)
AE (red). Aerobic conditions (exposure to the air)
AN (blue). Anaerobic conditions (not exposed to the air+antioxidants)

Figure 2:
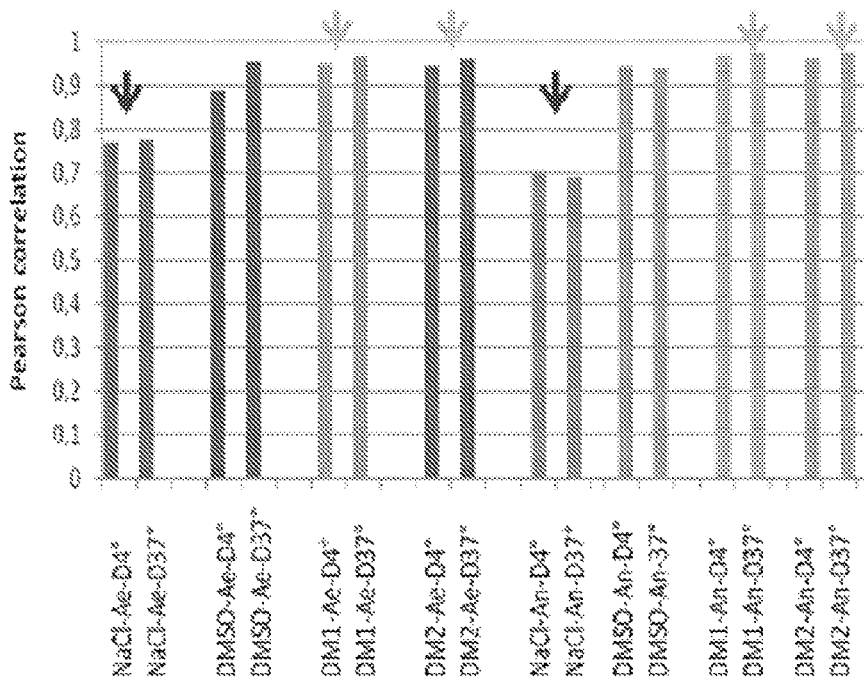

FIG. 2 results of the metabolimic analyses
DM1=MDX15
DM2=TR15

Figure 3:
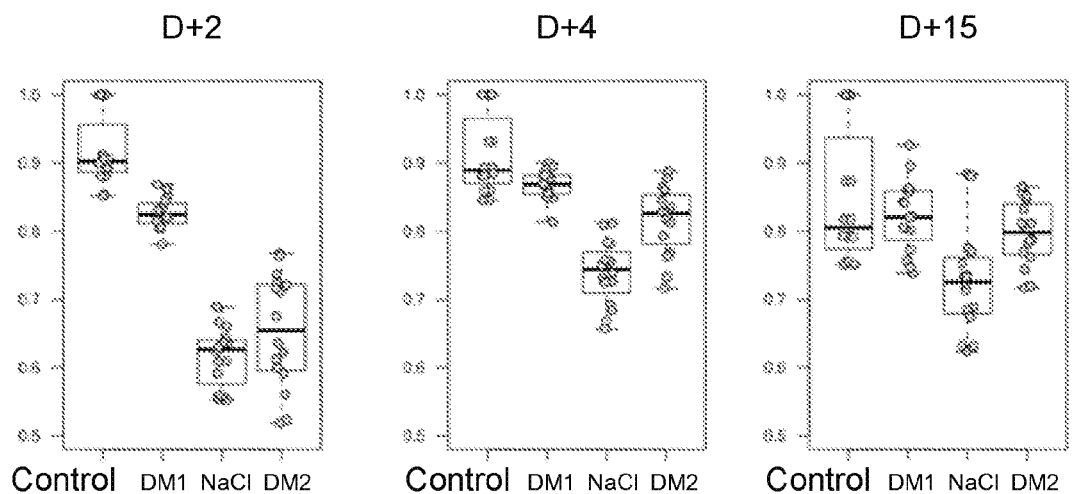

FIG. 3: Spearman correlations of bacterial genera for the different diluents tested after one week of storage, compared to the "fresh stools" control
DM1=MDX15
DM2=TR15

Figure 4:
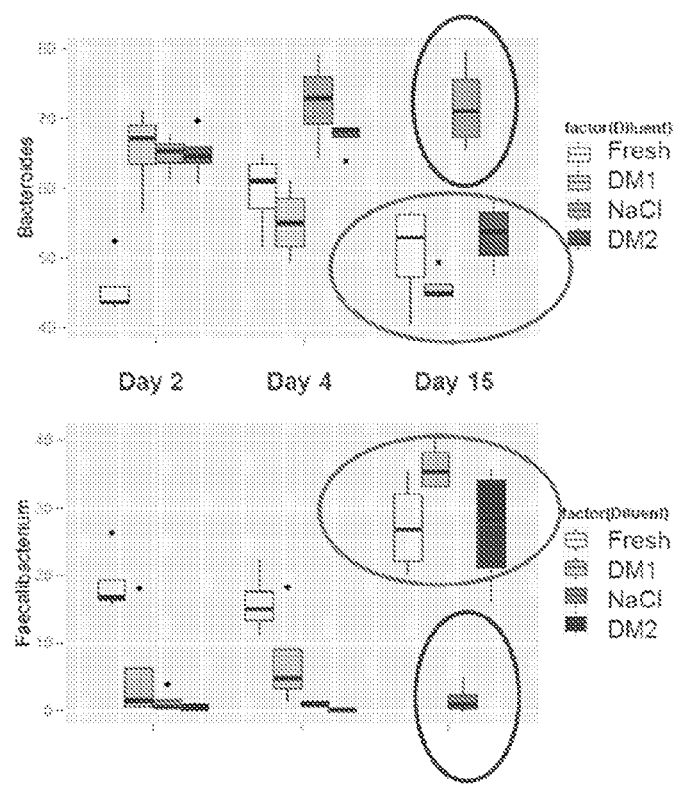

FIG. 4: colonization kinetics for populations of *Bacteroides* and *Faecalibacterium* in mouse faeces

EXAMPLE 1

Preparation of a Sample of Faecal *Microbiota* from a Donor Subject According to the Invention Materials and Methods:
The taking of samples Over three consecutive days, 3 participants (one per day) are invited to provide a sample of fresh stools, collected in the morning and placed under anaerobic conditions through the addition of a catalyst of the type Anaerocult® IS (ref 116819 from Merck-Millipore) (step a) of the method). A visual inspection and qualification of the stools are carried out according to the Bristol stool scale.

In the 2 h following collection, the stools are homogenized for 5 minutes in an anaerobic atmosphere, by manual kneading in the collection bag (step b) of the method). Small aliquots (150-200 mg) of untreated faecal material (US for Untreated Stool) are kept for 16S rDNA and 16S rRNA sequencing of the untreated faecal material. One aliquot (1 g) is diluted in cold enriched brain-heart broth, centrifuged at 220 000×g, at 4° C. for 1 h, and then the supernatant is divided up into aliquots of 1 ml for the metabolomic sequencing of untreated faecal water. The aliquots for the DNA, RNA and the metabolomic sequencing are stored at −80° C. A third aliquot (0.4 g) is diluted in 1.6 ml of culture broth and used to inoculate 3 Kimax culture tubes (0.5 ml of inoculum for 9.5 ml of broth, extemporaneously enriched with sodium L-ascorbate and L-cysteine hydrochloride monohydrate to a final concentration of 0.5% [w/v] and 0.05% [w/v], respectively) for the reference activity test.

Eight stool fractions are next transferred into Stomacher filter bags: 4 bags for processing in contact with four diluents under anaerobic conditions, and four bags for processing in the same four diluents under aerobic conditions.

Processing

Two teams perform the steps of processing in parallel to ensure that all the samples are treated identically.

The 4 fractions under each condition of atmosphere are put back in suspension in 4 volumes of the following aqueous solutions (step c) of the method):
Saline solution 9 g/L (identified as "NaCl"),
DMSO 6.25% (v/v) in a 9 g/L saline solution (identified as "DMSO"),
MDX (maltodextrins) 15% (w/v)+TR (trehalose) 5% (w/v) in a 9 g/L saline solution (identified as "MDX15"), and
MDX 5%+TR 15% in a 9 g/L saline solution (identified as "TR15"), The MDX15 and TR15 preparations made under anaerobic atmosphere are furthermore complemented with two reducing agents, sodium L-ascorbate and L-cysteine hydrochloride monohydrate, to a final concentration of 0.5% (w/v) and 0.1% (w/v), respectively.

Putting in suspension again is achieved by manual mixing for 5 minutes through the bag. This mixing achieves the filtration at the same time, through a gauze (holes of 0.5 mm) present in the bag (step d) of the method).

20 ml of each filtrate are then transferred with a pipette into two CryoMACS® Freezing Bags 50 (Ref Miltenyi Biotec SAS 200-074-400), giving a total of 16 CryoMACS® for each donor (2×NaCl-An, 2×DMSO-An, 2×MDX15-An, 2×TR15-An, 2×NaCl-Ae, 2×DMSO-Ae, 2×MDX15-Ae, 2×TR15-Ae), which are stored at −80° C. (step e) of the method).

Aliquots of each filtrate are also kept for the 16S rDNA and 16S rRNA, the metabolomic sequencing, and the bacterial cultures. For the 16S rDNA, 16S rRNA and the metabolomic sequencing, 6 aliquots of 1 ml of each suspension are centrifuged at 5000×g, 4° C. for 30 minutes, the supernatants grouped together are furthermore ultra-centrifuged (220 000×g, 4° C., 1 h) for the metabolomic sequencing, while the moist pellet from ×5000 g is kept for the 6S rDNA and 16S rRNA sequencing. Three aliquots of 0.5 ml from each filtrate are used to inoculate 3 Kimax culture tubes of culture broth, as described above for the untreated faecal material. The entire process is repeated 3 times over 3 consecutive days to manage 3 different stools from three different donors.

Reprocessing

To ensure the same storage time for the samples of the 3 donors, the CryoMACS bags are thawed over 3 consecutive days at the rate of one bag per person per day. The thawing is carried out using two different protocols (step f) of the method):

for one night at 4° C.;

for 5 minutes at 37° C. in a water bath.

After thawing, the samples are placed in culture in an enriched brain-heart broth, and the metabolic activity is measured. The filtrate aliquots thawed before culture (non-cultured thawed filtrates) are also kept for the 16S rDNA, 16S rRNA and the metabolomic sequencing.

The Microbial Cultures

At each critical step of the method, a sample is collected and used to seed culture tubes in triplicate each containing 9.5 mL of enriched brain-heart broth. The culture tubes had already been reduced in the anaerobic chamber to eliminate all dissolved dioxygen and enable the strictly anaerobic growth of the bacteria.

After incubation for 48 hours at 37° C. under strict anaerobic conditions, the cultures in triplicate are harvested, grouped together in Falcon50 tubes, and centrifuged for 30 min at 5000×g, 4° C. The supernatant is furthermore ultra-centrifuged for 1 hour at 220 000×g, 4° C. for the metabolomic sequencing (1 ml of supernatant fraction kept at −80° C.), while the moist pellet from 5000×g is divided into three equal fractions in Sarstedt tubes for the 6S rDNA and 16S rRNA, all the aliquots being kept at −80° C. until analysis.

Metabolomic Analyses

The metabolomic analyses are then carried out, to obtain the LC-MS profiles (Q-Exactive Thermofisher Scientific) in positive and negative ionization modes.

Phylogenetic Profile

The whole DNA is extracted. It is then checked and sequenced by pyrosequencing.

Transcriptome Sequencing

The RNA is extracted by using the following method: briefly, the bacteria are lysed by chemical and mechanical treatment; then the lysates are precipitated and centrifuged; lastly the RNA is isolated and purified on minicolumns using the High Pure Isolation Kit (Roche). Their integrity is evaluated and they are next subjected to an RT-PCR. The cDNA are sequenced by pyrosequencing, then subjected to the same analysis as for the DNA.

Results:

Phylogenetic Profile

The major discriminating factor is the subject. This was expected, given that the specificity of the host of the microbial flora is well-established. This means that whatever the effect of processing on the stools, it will satisfy the specificity of the host.

The comparisons made will thus be reliable and the behaviors maintained for different individuals will be more significant.

The Pearson and Spearman correlations were next used to evaluate the most effective diluent for processing. Similar observations were made when comparing the phylogenetic profiles based on the whole DNA and the phylo-transcriptome sequencing based on the RNA. The illustration below (FIG. 1) highlights the main results obtained.

Impact of the Reprocessing Procedure on the Integrity of the Sample

The conditions compared for the re-processing of the frozen preparations which must be used for re-administration are:

for one night at 4° C.; or for 5 minutes at 37° C.

Whatever the diluent (MDX15 or TR15), the fast thawing at 37° C. appears the most favorable for reconstituting a microbiota close to the initial stools.

Transcriptome Sequencing

The Pearson correlations between the phylo-transcriptome profiles are discriminating and informative, whereas between the phylo-genomic profiles they are not.

FIG. 1 presents the Pearson correlations between the phylo-transcriptomic profiles obtained on the basis of the distribution with regard to bacterial families in the total RNA of the different fractions prepared. The reference is the profile obtained from untreated faecal material (US for 'Untreated Stool').

The Figure indicates that the diluents containing the mixtures of maltodextrin (MDX) and trehalose (TR) enable a better preservation of the integrity of the dominant microbiota relative to the saline solution (NaCl). Since then, similar observations have been made for DNA, which means that the method enables the populations and their functional integrity to be preserved.

Metabolomic Analyses

The results of the metabolomic analyses are presented in FIG. 2.

The metabolic profiles of the cultures of thawed faecal suspensions in MDX15 or TR15 are the most similar to the cultures of the corresponding fresh suspensions (green arrows), whether under aerobic (Ae) or anaerobic (An) conditions. Weaker correlations were obtained between the cultures of frozen and fresh suspensions in NaCl (red arrows). The re-processing at 4° C. overnight or at 37° C. for 5 minutes makes little difference to the metabolomic profile.

Overall, on the basis of the preservation of the metabolic profiles between the cultures of fresh faecal material, suspensions of fresh faecal material and the same frozen-unfrozen suspensions, maltodextrins or trehalose are cryoprotectant and bulking agents that are very effective for faecal transplantations.

EXAMPLE 2

Reconstruction of the Microbiota in Germ-Free Mice

The method is directed to analyzing the impact of the processing of human stools on the intestinal ecology reconstructed after inoculation into germ-free mice of the line C3H/HeN. The standardized approach comprises a control group and several test groups. In comparison to the control group receiving a suspension of freshly collected stools, the test groups receive preparations made from the same stools:
  frozen in NaCl,
  frozen with 15% maltodextrins and 5% trehalose ("MDX15" described in example 1); or
  frozen with 15% trehalose and 5% maltodextrins ("TR15" described in example 1).

These various conditions are directed to optimizing the preservation of the microbiota.

The frozen fractions are administered in vivo after processing and storage for 1 to 7 weeks. A test control was made with untreated stool formulated in NaCl, implanted immediately after processing. This procedure makes use of germ-free mice receiving the different preparations of inoculum per os, using an oro-gastric probe (0.2 mL/mouse). The evaluation of the success of the procedure is based on the characterization of the microbiota in terms of composition and activity, maximum similarity (%) with the control being sought initially. This procedure is implemented on 4 animals per condition to test a set of conditions validated in advance by comparative analyses in vitro.

Sampling and analyses: after 2 days, 4 days and 15 days, 2 to 3 freshly and spontaneously evacuated pellets are collected per animal in the morning for microbiological analysis. Furthermore, a sample of ceacal content is collected through killing at 15 days for phylogenomic and/or transcriptomic and metabolomic analysis.

Results:

These analyses were conducted on the first series of cages (1 week of preservation vs control). The DNA was extracted then sequenced in terms of rDNA 16S. The OTUs (Operational Taxonomic Units) were identified and quantified. A Spearman statistical correlation next enables the taxonomic contents of each sample tested to be compared. The results are presented in FIG. 3.

The Spearman correlations calculated between the different conditions show that colonization is made effectively with an advantage for the DM1 and DM2 formulations compared with 0.9% NaCl alone. At D+2, the DM1 formulation bears very close similarities to the controls, whereas the DM2 formulation attains a performance level equivalent at D+4. At D+4, the microbiota stabilizes and little difference is observed with the point D+15.

An in-depth analysis relating to the bacterial genera most affected in these tests, that is to say the genera *Bacteroides* and *Faecalibacterium*, is presented in FIG. 4.

The change from D2 to D15 clearly shows that the DM1 diluent rapidly presents a profile closer to the fresh stool than the DM2 diluent. At 15 days however, both have similar profiles. By contrast, NaCl promote strong colonization by *Bacteroides*, which are pro-inflammatory bacteria, to the detriment in particular of *Faecalibacterium*, which practically fail to implant. As a matter of fact, the genus *Faecalibacterium* has been greatly studied since it presents anti-inflammatory properties and contributes to the effectiveness of the intestinal barrier (Everard, 2013; Sokol, 2008). Its presence in a small amount in the human microbiota also correlates with different pathologies (Crohn's disease, obesity, inflammatory diseases of the intestine, etc.).

The use of NaCl does not therefore enable a flora of the same quality to be established as the fresh initial stool, whereas the diluents DM1 and DM2 do achieve this, with a slightly faster effect with DM1, as well as a smaller inter-individual variability, represented by the height of the box.

The development of the distribution of the bacterial families follows a same tendency between the control group, the group which received the sample with MDX15 (DM1) and the group which received the sample with TR15 (DM2).

The same tendency is observed on the samples and analyses carried out after 7 weeks of storage (results not shown).

It is thus shown that Maltodextrins or Trehalose Enable Effective Recolonization of the Intestine without Alteration of the Initial Microbiota.

Everard, A., 2013. Cross-talk between Akkermansia muciniphila and intestinal epithelium controls diet-induced obesity. *Proc Natl Acad Sci USA*, pp. 110(22): 9066-71.

Sokol, H., 2008. *Faecalibacterium prausnitzii* is an anti-inflammatory commensal bacterium identified by gut microbiota analysis of Crohn disease patients. *Proc Natl Acad Sci USA*, pp. 105(43):16731-6.

The invention claimed is:

1. A method of preparing a sample of faecal microbiota from a donor subject, comprising the following steps:
   a) taking at least one sample of faecal microbiota from the donor subject,
   b) within 5 minutes following taking of the sample, placing said sample obtained in a) in an oxygen-tight collecting device,
   c) mixing the sample obtained in b) with at least one saline aqueous solution comprising 5-1.5% w/v of at least one cryoprotectant selected from the group consisting of trehalose, galactose-lactose and combinations thereof; and 5-15% w/v of at least one maltodextrin to form a mixture,
   d) optionally, filtering the mixture obtained in c), and
   e) storing the mixture obtained in c) or d) by freezing at a temperature between −1.5° C. and −100° C.,
   wherein steps b) to e) are carried out under anaerobiosis and wherein bacterial functional integrity of the faecal microbiota is preserved, and
   wherein the at least one saline aqueous solution further comprises sodium ascorbate and cysteine hydrochloride monohydrate.

2. The method of claim 1, wherein the sample placed in the collecting device of step b) undergoes a transportation step prior to step c).

3. The method of claim 1, wherein the sample placed in the collecting device of step b) is incubated at a temperature comprised between 33° C. and 40° C. for a maximum time of 75 h, between steps b) and c).

4. The method of claim 1, wherein the saline aqueous solution comprises:
   at least one salt chosen from sodium chloride, calcium chloride, magnesium chloride, potassium chloride, sodium gluconate and sodium acetate.

5. The method of claim 1, wherein the at least one maltodextrin is a mixture of maltodextrins.

6. The method of claim 1, further comprising a step f) of thawing the frozen sample obtained in e), under anaerobiosis, up to ambient temperature.

7. A method for transplantation of autologous or allogenic faecal *Microbiota*, comprising introducing by transplantation into a subject the thawed sample of donor fecal *Microbiota* prepared according to the method of claim 6.

8. A method for treating intestinal dysbioses, comprising introducing by transplantation into a patient in need thereof the thawed sample of donor fecal *Microbiota* prepared according to the method of claim 6.

9. The method of claim 1, wherein the filter used in step d) comprises pores of diameter less than or equal to 0.7 mm.

10. The method of claim 1, wherein the filter used in step d) comprises pores of diameter less than or equal to 0.5 mm.

11. The method of claim 1, wherein freezing in step e) is at a temperature between −60° C. and −90° C.

12. The method of claim 1; where the at least one saline aqueous solution comprises 0.5% w/v sodium L-ascorbate and 0.1% w/v cysteine hydrochloride monohydrate.

13. The method of claim 1, wherein the amount of cryoprotectant and maltodextrin in the at least one saline aqueous solution is 20% w/v.

14. The method of claim 13, wherein the amount of cryoprotectant is 15% w/v trehalose, galactose-lactose or a combination thereof and the amount of maltodextrin is 5% w/v.

15. The method of claim 13, wherein the amount of cryoprotectant is 5% w/v trehalose, galactose-lactose or a combination thereof and the amount of maltodextrin is 15% w/v.

\* \* \* \* \*

UNITED STATES PATENT AND TRADEMARK OFFICE
CERTIFICATE OF CORRECTION

| | |
|---|---|
| PATENT NO. | : 10,980,839 B2 |
| APPLICATION NO. | : 15/568838 |
| DATED | : April 20, 2021 |
| INVENTOR(S) | : Hervé Affagard et al. |

It is certified that error appears in the above-identified patent and that said Letters Patent is hereby corrected as shown below:

In the Claims

Claim 1, Column 12, Line 42, delete "1.5%" and insert therefor --15%--

Signed and Sealed this
Seventeenth Day of May, 2022

Katherine Kelly Vidal
*Director of the United States Patent and Trademark Office*